(12) United States Patent
Luan et al.

(10) Patent No.: US 8,603,303 B2
(45) Date of Patent: Dec. 10, 2013

(54) NANOPORE BASED DEVICE FOR CUTTING LONG DNA MOLECULES INTO FRAGMENTS

(75) Inventors: Binquan Luan, Ossining, NY (US); Glenn J. Martyna, Croton-on-Hudson, NY (US); Hongbo Peng, Yorktown Heights, NY (US); Gustavo A. Stolovitsky, Riverdale, NY (US)

(73) Assignee: International Business Machines Corporation, Armonk, NY (US)

( * ) Notice: Subject to any disclaimer, the term of this patent is extended or adjusted under 35 U.S.C. 154(b) by 598 days.

(21) Appl. No.: 12/723,842

(22) Filed: Mar. 15, 2010

(65) Prior Publication Data
US 2011/0224098 A1    Sep. 15, 2011

(51) Int. Cl.
*C07H 21/04* (2006.01)
*B01J 19/08* (2006.01)

(52) U.S. Cl.
USPC ............ 204/157.68; 204/157.15; 977/781; 506/43

(58) Field of Classification Search
None
See application file for complete search history.

(56) References Cited

U.S. PATENT DOCUMENTS

| | | | |
|---|---|---|---|
| 4,692,992 A | 9/1987 | Hsu | |
| 5,671,086 A | 9/1997 | Parvin et al. | |
| 6,180,490 B1 | 1/2001 | Vassiliev et al. | |
| 6,217,872 B1 | 4/2001 | Okayama et al. | |
| 6,413,792 B1 | 7/2002 | Sauer et al. | |
| 6,627,067 B1 * | 9/2003 | Branton et al. | ............... 205/778 |
| 7,282,130 B2 | 10/2007 | Flory | |
| 7,347,921 B2 | 3/2008 | Barth et al. | |
| 7,468,271 B2 | 12/2008 | Golovchenko et al. | |
| 7,540,717 B2 | 6/2009 | Sheng et al. | |
| 7,846,738 B2 | 12/2010 | Golovchenko et al. | |
| 2005/0019784 A1 | 1/2005 | Su et al. | |
| 2005/0101100 A1 | 5/2005 | Kretchmer et al. | |
| 2005/0110990 A1 | 5/2005 | Koo et al. | |
| 2005/0158763 A1 | 7/2005 | Ivanisevic et al. | |
| 2006/0105553 A1 | 5/2006 | Wellhausen | |
| 2006/0154399 A1 | 7/2006 | Sauer et al. | |
| 2006/0169588 A1 | 8/2006 | Jacobson et al. | |
| 2006/0180469 A1 | 8/2006 | Han et al. | |

(Continued)

FOREIGN PATENT DOCUMENTS

| | | |
|---|---|---|
| EP | 0261592 A1 | 9/1987 |
| EP | 1441213 | 7/2004 |

(Continued)

OTHER PUBLICATIONS

U.S. Appl. No. 12/820,543, filed Jun. 22, 2012; First Named Inventor: Ali Afzali-Ardakani.

(Continued)

*Primary Examiner* — Christopher M Gross
(74) *Attorney, Agent, or Firm* — Cantor Colburn LLP; Vazken Alexanian

(57) ABSTRACT

Apparatus, system, and method are provided for cutting a linear charged polymer inside a nanopore. A first voltage is applied to create an electric field in a first direction. A second voltage is applied to create an electric field in a second direction, and the first direction is opposite to the second direction. When the electric field in the first direction and the electric field in the second direction are applied to a linear charged polymer inside a nanopore, the linear charged polymer is cut at a location with predetermined accuracy.

8 Claims, 5 Drawing Sheets

(56) References Cited

U.S. PATENT DOCUMENTS

| | | |
|---|---|---|
| 2006/0246497 A1 | 11/2006 | Huang et al. |
| 2007/0020146 A1 | 1/2007 | Young et al. |
| 2007/0048745 A1 | 3/2007 | Joyce et al. |
| 2007/0138132 A1 | 6/2007 | Barth |
| 2007/0187694 A1 | 8/2007 | Pfeiffer |
| 2007/0190542 A1 | 8/2007 | Ling et al. |
| 2008/0003571 A1 | 1/2008 | McKernan et al. |
| 2008/0032290 A1 | 2/2008 | Young |
| 2008/0102504 A1 | 5/2008 | Akeson et al. |
| 2008/0119366 A1 | 5/2008 | Sauer et al. |
| 2008/0171316 A1 | 7/2008 | Golovchenko et al. |
| 2008/0187915 A1 | 8/2008 | Polonsky et al. |
| 2008/0257859 A1 | 10/2008 | Golovchenko et al. |
| 2009/0136958 A1 | 5/2009 | Gershow et al. |
| 2009/0188794 A1 | 7/2009 | Simon et al. |
| 2009/0221443 A1 | 9/2009 | Heller et al. |
| 2009/0222216 A1 | 9/2009 | Hibbs et al. |
| 2010/0025249 A1 | 2/2010 | Polonsky et al. |
| 2010/0084276 A1 | 4/2010 | Lindsay |
| 2010/0327255 A1 | 12/2010 | Peng et al. |
| 2010/0327847 A1 | 12/2010 | Leiber et al. |
| 2010/0331194 A1* | 12/2010 | Turner et al. ............... 506/2 |
| 2011/0052813 A1 | 3/2011 | Ho et al. |
| 2011/0220574 A1 | 9/2011 | Bakajin et al. |
| 2011/0236984 A1 | 9/2011 | Sun et al. |
| 2011/0279125 A1 | 11/2011 | Bedell et al. |
| 2012/0146162 A1 | 6/2012 | Cho et al. |

FOREIGN PATENT DOCUMENTS

| | | |
|---|---|---|
| EP | 1486775 A | 12/2004 |
| WO | WO0181908 A | 11/2001 |
| WO | WO2006122317 | 11/2006 |
| WO | WO2007084163 A | 7/2007 |
| WO | WO2008051308 A2 | 5/2008 |
| WO | WO2008132643 A1 | 11/2008 |
| WO | WO2009032756 A2 | 3/2009 |

OTHER PUBLICATIONS

Hongbo Peng, et al., pending U.S. Appl. No. 13/359,729, entitled "Electron Beam Sculpting of Tunneling Junction for Nanopore DNA Sequencing," filed with the U.S. Patent and Trademark Office on Jan. 27, 2012.
Hongbo Peng, et al., pend U.S. Appl. No. 13/359,743, entitled "DNA Motion Control Based on Nanopore with Organic Coating Forming Transient Bonding to DNA," filed with the U.S. Patent and Trademark Office on Jan. 27, 2012.
Hongbo Peng, et al., pending U.S. Appl. No. 13/359,750, entitled "DNA Sequencing Using Multiple Metal Layer Structure with Organic Coatings Transient Bonding to DNA Bases," filed with the U.S. Patent and Trademark Office on Jan. 27, 2012.
Hong Peng, et al., pending U.S. Appl. No. 13/359,766, entitled "DNA Sequencing Using Multiple Metal Layer Structure with Different Organic Coatings Forming Different Transient Bondings to DNA," filed with the U.S. Patent and Trademark Office on Jan. 27, 2012.
A. Bergvall et al., "Graphene nanogap for gate-tunable quantum-coherent single-molecule electronics," Phys. Rev. B, vol. 84, No. 15, 2011, 155451, 7 pages.
B. Loan et al., "Tribological Effects on DNA Translocation in a Nanochannel Coated with a Self-Assembled Monolayer," J. Phys. Chem. B, vol. 114, 2010, pp. 17172-17176; Nov. 12, 2010.
Bae, S. et al., "Roll-to-Roll Production of 30-inch Graphene Films for Transparent Electrodes," Nature Nanotechnology, Published online: Jun. 20, 2010, 5 pages.
I. Braslavsky, B. Hebert, E. Kartalov, S. R. Quake, "Sequence Information Can Be Obtained from Single DNA Molecules," Proc. Natl. Acad. Sci. USA, vol. 100, pp. 3960-3964 (2003).
F. S. Collins, M. Morgan, A. Patrinos, "The Human Genome Project—Lessons From Large-scale Biology," Science, vol. 300, pp. 286-290 (2003).

M. Fedurco, A. Romieu, S. Williams, I. Lawrence, G. Turcatti, "BTA, a Novel Reagent for DNA Attachment on Glass and Efficient Generation of Solid-phase Amplified DNA Colonies," Nucleic Acids Res. vol. 34, pp. e22 (2006).
A. K. Geim and K. S. Novoselov, "The Rise of Graphene," Nature Materials 6, 183 (2007), 9 pages.
S. Harrer et al. "Electrochemical Characterization of Thin Film Electrodes Towards Developing a DNA-Transistor," Langmuir, vol. 26 (24), pp. 19191-19198 (2010).
S. Harrer et al., "Electrochemical Protection of Thin Film Electrodes in Solid State Nanopore," Nanotechnology, vol. 22, 2011, 275304, 6 pages
T. D. Harris et al., "Single-molecule DNA Sequencing of a Viral Genome," Science, vol. 320, pp. 106-109 (2008).
J- Hass, W.A. De Heer and E.H. Conrad, "The Growth and Morphology of Epitaxial Multilayer Graphene," Journal of Physics: Condensed Matter 20, 323202 (2008), 28 pages.
H.W.C Postma, "Rapid Sequencing of Individual DNA Molecules in Graphene Nanogaps," Nano Letters, vol. 10, No. 2, Jan. 4, 2010, pp. 420-425.
J. Prasongkit et al., "Transverse conductance of DNA necleotides in a graphene nanogap from first principles," arXiv:1012.1669v2 [physics.ins-det], [v1] Dec 8, 2010, [v2] Jan. 14, 2011, Nano Lett., vol. 11, No. 5, 2011, pp. 1941-1945.
J. J. Kasianowicz, E. Brandin, D. Branton, D. W. Deamer, "Characterization of Individual Polynucleotide Molecules Using a Membrane Channel," Proc. Natl. Acad. Sci. USA., vol. 93, pp. 13770-13773 (1996).
K.S. Kim, Y. Zhao, H. Jang, S. Y. Lee, J. M. Kim, K. S. Kim, J. H. Ahn, P. Kim, J. Y. Choi, B. H. Hong, "Large-Scale Pattern Growth of Graphene Films for Stretchable Transparent Electrodes," Nature 457, 706-710 (2009).
B. Luan, H. Peng, S. Polonsky, S. Rossnagel, G. Stolovitzky, and G. Martyna, "Base-by-base Ratcheting of Single-stranded DNA Through a Solid-state Nanopore," Phys. Rev. Lett., vol. 104 (23) pp. 238103-1-238103-4 (2010).
B. Luan, A. Aksimentiev, "Control and Reversal of the Electrophoretic Force on DNA in a Charged Nanopore," J. Phys. Condens. Matter, vol. 22, pp. 454123 (2010).
B. Luan et al., "Tribological Effects on DNA Translocation in a Nanochannel Coated with a Self-Assembled Monolayer," J. Phys. Chem. B, vol. 114, 2010, pp. 17172-17176.
M. Margulies et al., "Genome Sequencing in Mircrofabricated High-density Pico-litre Reactors," Nature, vol. 437, pp. 376-380 (2005).
Meller A., Nivon L., Brandin E., Golovchenko J. and Branton D., "Rapid Nanopore Discrimination Between Signle Polynucleotide Molecules," Proc. Natl Acad. Sci. USA 97 1079-84 (2000).
Novoselov K S et al, "Electric Field Effect in Atomically Thin Carbon Films" Science, American Association for the Advancement of Science, US, Washington, DC, vol. 306, No. 5696, Oct. 11, 2004, pp. 666-669, XP009086357, ISSN: 0036-8075, the whole document.
Fernando Patolsky, Gengfeng Zheng, Oliver Hayden, Melike Lakadamyali, Xiaowei Zhuang, and Charles M. Lieber, "Electrical detection of single viruses," Departments of Chemistry and Chemical Biology and Physics and Division of Engineering and Applied Sciences, Harvard University, Cambridge, MA 02138, Contributed by Charles M. Lieber, Aug. 20, 2004, pp. 1-6.
F. Sanger, S. Nicklen, A. R. Coulson, "DNA sequencing with chain termination inhibitors," Proc. Natl. Acad. Sci USA., vol. 74 (12), pp. 5463-5467 (1977).
Schedin F et al: "Detection of Individual Gas Molecules Absorbed on Graphene" Nature Materials Nature Publishing Group, UK, vol. 6, No. 9, Sep. 2007, pp. 652-655, XP002506772, ISSN: 1476-1122, the whole document.
J. Shedure et al., "Accurate Multiplex Polony Sequencing of an Evolved Bacterial Genome," Science, vol. 309, pp. 1728-1732 (2005).
A. Sidorenko et al., "Controlled Switching of the Wetting Behavior of Bioimetic Surfaces with Hydrogel-Supported Nanostructures," J. Mater. Chem., vol. 18, 2008, pp. 3841-3846.
Soni G and Meller A, "Progress Towards Ultrafast DNA Sequencing Using Solid State Nanopores," Clin. Chem. 3 Jan. 1996 (2007), 6 pages.

(56) References Cited

OTHER PUBLICATIONS

Eric Stern, James F. Klemic, David A. Routenberg, Pauline N. Wyrembak, Daniel B. Turner-Evans, Andrew D. Hamilton, David A. Lavan, Tarek M. Fahmy and Mark A. Reed, "Label-free immunodetection with CMOS-compatible semiconducting nanowires," Nature Publishing Group, vol. 445, Feb. 2007, doi:10.1038/nature05498, pp. 1-4.

A. J. Storm, J. H. Chen, X. S. Ling, H. W. Zandbergen and C. Dekker, "Fabrication of Solid-State Nanopores with Single-Nanometre Precision," Nature Materials 2, 537-540 (2003).

G. Tizazu et al.' "Photopatterning, Etching, and Derivatization of Self-Assembled Monolayers of Phosphonic Acids on the Native Oxide of Titanium," Langmuir, vol. 25, 2009, pp. 10746-10753.

G. Turcatti, A. Romieu, M. Fedurco, A. P. Tairi, "A New Class of Cleavable Fluorescent Nucleotides: Synthesis and Optimization as Reversible Terminators for DNA Sequencing by Synthesis," Nucleic Acids Res., vol. 36, pp. e25 (2008).

U.S. Appl. No. 12/820,543, filed Jun. 22, 2010; Title: Forming an Electrode Having Reduced Corrosion and Water Decomposition on Surface Using an Organic Protective Layer; Harrer et al.

S. Vassanelli, P. Fromherz, "Transistor Probes Local Potassium Conductances in the Adhesion Region of Cultured Rat Hippocampal Neurons," The Journal of Neuroscience, Aug. 15, 1999, 19(16):6767-6773, Department of Membrane and Neurophysics, Max-Planck-Institute for Biochemistry.

G. Wang et al., "Photon Gated Transport at the Glass Nanopore Electrode," J. Am. Chem. Soc., vol. 128, 2006, pp. 13553-13558.

B. Luan et al., "Dna-translocation through a solid state nanopore coated with a self-assembled monolayer," Bull. Am. Phys. Soc., APS March Meeting 2011, vol. 56, No. 1, Abstract V43.00002, Mar. 24, 2011, 1 page.

Amit Meller et al., "Rapid nanopore discrimination between single polynucleotide molecules," PNAS, Feb. 1, 2000, vol. 97, No. 3, pp. 1079-1084.

Akeson, Mark, et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77, Dec. 1999, pp. 3227-3233.

Branton, Daniel, et al., "The potential and challenges of nanopore sequencing" NIH Public Access—Author Manuscript, Nat Biotechnol. available in PMC May 18, 2009, pp. 1-17.

Gracheva, Maria E. et al., "Simulation of the electric response of DNA translocation through a semiconductor nanopore—capacitor", Institute of Physics Publishing, Nanotechnology, vol. 17 (2006), pp. 622-633.

Heng, Jiunn B. et al., "Sizing DNA Using a Nanometer-Diameter Pore", Biophysical Journal, vol. 87, Oct. 2004, pp. 2905-2911.

Kasianowicz, John J., et al., "Characterization of individual polynucleotide molecules using a membrane channel", Proc. Natl. Acad. Sci. USA, vol. 93, Nov. 1996, pp. 13770-13773.

Lagerqvist, Johan et al., "Fast DNA Sequencing via Transverse Electronic Transport", Nano Lett., vol. 6, No. 4, Received Jan. 17, 2006; revised Manuscript Received Mar. 1, 2006, pp. 779-782.

Soni, Gautam V. et al., "Progress toward Ultrafast DNA Sequencing Using Solid-State Nanopores", Clinical Chemistry, vol. 53, No. 11, (2007), pp. 1-6.

Polonsky et al., "Nanopore in metal-dielectric sandiwch for DNA position control," Applied Physics Letters 91, 153103 (2007).

Douville, et al., "DNA Linearization Through Confinement in Nanofluidic Channels, Anal Bioanal Chem", Aug. 2008; vol. 391; No. 7; pp. 2395-2409; Abstract; pg. 2402, col. 2; para 5; p. 2406; col. 2; para 2; p. 2407; Fig. 5b.

International Search Report—PCT; Notification of Transmittal of the International Search Report and The Written Opinion of the International Searching Authority, or the Declaration; Apr. 5, 2011; International application No. PCT/US1123872.

United States Patent and Trademark Office, Non-Final Office Action for U.S. Appl. No. 12/704,665 received Mar. 16, 2011; pp. 1-15.

Written Opinion of the International Searching Authority; date of mailing Apr. 5, 2011; pp. 1-6; International application No. PCT/US11/23872.

* cited by examiner

FIG. 3

Apply a first voltage to create an electric field in a first direction 302

↓

Apply a second voltage to create an electric field in a second direction, where the first direction is opposite to the second direction 304

↓

When the electric field in the first direction and the electric field in the second direction are applied to a polymer inside a nanopore, cause the linear charged polymer to be cut at a precise location 306

NANOPORE BASED DEVICE FOR CUTTING LONG DNA MOLECULES INTO FRAGMENTS

This application contains subject matter which is related to the subject matter of the following co-pending application, which is assigned to the same assignee as this application: International Business Machines Corporation of Armonk, N.Y.; and the below listed application is incorporated herein by reference in its entirety: PIEZOELECTRIC-BASED NANOPORE DEVICE FOR THE ACTIVE CONTROL OF THE MOTION OF POLYMERS THROUGH THE SAME, filed Mar. 15, 2010, application Ser. No. 12/723,724.

BACKGROUND

Exemplary embodiments relate to nanodevices, and more specifically, to a nanopore device for cutting polymers.

Recently, there has been growing interest in applying nanopores as sensors for rapid analysis of biomolecules (DNA, RNA, protein, etc). Special emphasis has been given to applications of nanopores for DNA sequencing, as this technology holds the promise to reduce the cost of sequencing below $1000/human genome. An issue in these applications is the control of the translocation of DNA through the nanopore.

Nanopore sequencing is a method for determining the order in which nucleotides occur on a strand of DNA. A nanopore is simply a small hole of the order of several nanometers in internal diameter. The theory behind nanopore sequencing has to do with what occurs when the nanopore is immersed in a conducting fluid and an electric potential (voltage) is applied across it: under these conditions a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be put around the nanopore so that DNA bases can be differentiated while the DNA passes through the nanopore.

DNA could be driven through the nanopore by using various methods. For example, an electric field might attract the DNA towards the nanopore, and it might eventually pass through it. Also, enzymes attached to the nanopore might guide DNA towards the nanopore. The scale of the nanopore means that the DNA may be forced through the hole as a long string, one base at a time, rather like thread through the eye of a needle.

BRIEF SUMMARY

According to one exemplary embodiment, a method is provided for cutting a linear charged polymer inside a nanopore. A first voltage is applied to create an electric field in a first direction. A second voltage is applied to create an electric field in a second direction, and the first direction is opposite to the second direction. When the electric field in the first direction and the electric field in the second direction are applied to a linear charged polymer inside a nanopore, the linear charged polymer is caused to be cut at a location with a specified precision.

Other systems, methods, apparatus, design structures, and/or computer program products according to embodiments will be or become apparent to one with skill in the art upon review of the following drawings and detailed description. It is intended that all such additional systems, methods, apparatus, design structures, and/or computer program products be included within this description, be within the scope of the exemplary embodiments, and be protected by the accompanying claims. For a better understanding of the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features are apparent from the following detailed description taken in conjunction with the accompanying drawings in which:

FIG. 3 illustrates a method of cutting a polymer in accordance with exemplary embodiments.

DETAILED DESCRIPTION

Figure 1:
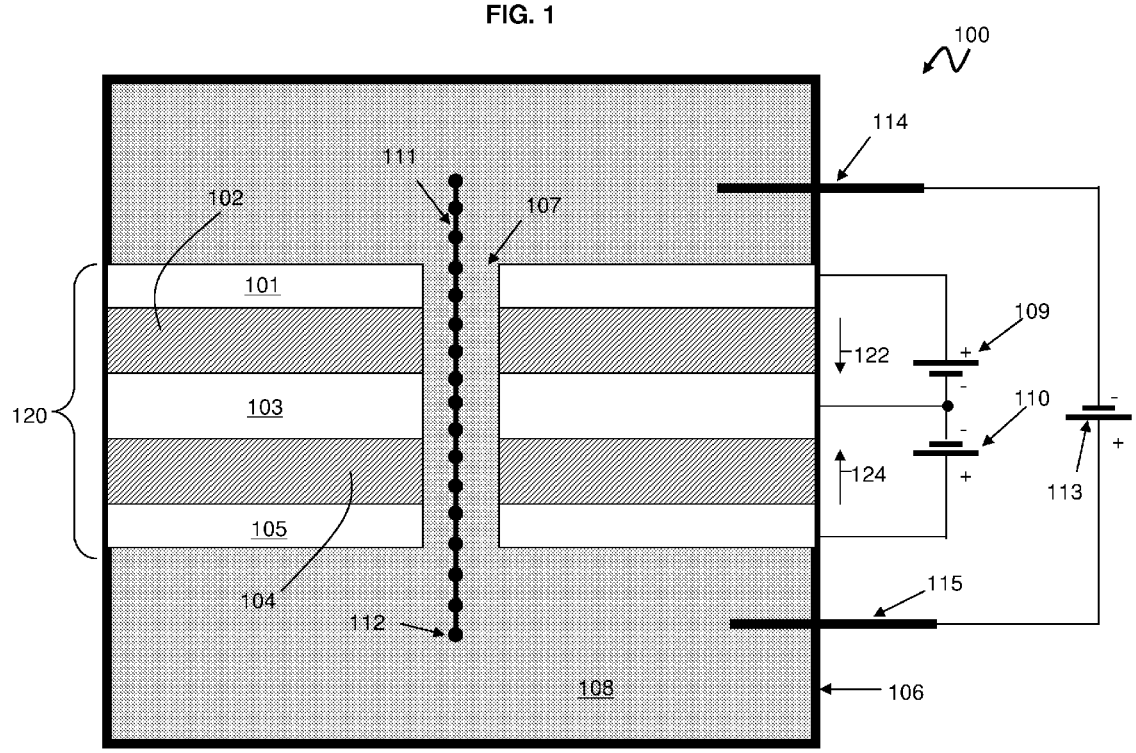
FIGS. 1 and 2 illustrate a schematic of a nanopore device in accordance with exemplary embodiments.

Exemplary embodiments provide a method and mechanism to perform DNA restriction, which is a process whereby a long DNA molecule is cut into shorter fragments.

Unlike exemplary embodiments, conventional fragmentation methods can be physical (e.g., nebulization, sonication and hydrodynamic shearing) or enzymatic. Enzymatic restriction is achieved using an enzyme that recognizes and cuts DNA molecules at specific sequence patterns (restriction sites). DNA restriction is routinely used in preparation of samples. Many applications such as chip-on-chip and DNA sequencing, from the original Sanger sequencing to most large-scale DNA sequencing strategies, require the fragmentation of the DNA to be sequenced for sub-cloning and further processing. In these applications, a long DNA molecule containing tens of thousands of bases must be cut into shorter fragments with a typical length of 100 to 1000 bases. Both in the physical as well as enzymatic fragmentation methods DNA fragments have a variable length whose distribution depends on the method used for fragmentation. In the sequencing applications, producing many short DNA fragments would increase the cost of sequencing, while producing long DNA fragments could potentially reduce the accuracy of sequencing.

In order to optimize the outcome in these applications, it might be desirable to produce a library of DNA fragments with a prescribed length utilizing the DNA transistor described in the patent application "Systems and methods for controlling the position of a charged polymer inside a nanopore", U.S. patent publication number 2008/0187915 (now U.S. Pat. No. 8,003,319) which is herein incorporated by reference. The DNA transistor is a device that allows for the controlled translocation of DNA molecules though a solid nanopore at a single-nucleotide resolution. A DNA transistor contains a metal-dielectric-metal-dielectric-metal multi-layered solid membrane and a few nanometer sized pore drilled through such solid membrane. When properly chosen voltages are applied to the metal layers, DNA can be effectively trapped within the DNA transistor. The voltage applied to the metal layers produces an electric field that effectively traps DNA molecule. Switching on and off such voltages in the presence of a biasing field corresponds to stopping and moving states of DNA, respectively. Since the DNA molecule translocates at a rate of one nucleotide per cycle of on-off voltages on the electrodes of the DNA transistor, it is possible to count the number of bases that translocate through the pore.

In accordance with exemplary embodiments, after a desired number of DNA bases have translocated, the DNA molecule can be stopped by applying the trapping potential for a period of time. Under this condition, DNA can be electrically stretched and broken into two pieces at a pre-determined location within the DNA transistor using the features described herein in accordance with exemplary embodiments. After cutting the DNA according to exemplary embodiments, the short DNA fragment can be electrically driven through the nanopore to exit the membrane, while the rest of the long DNA fragment continues moving forward base by base to start a new cutting cycle.

In exemplary embodiments, it is possible to cut sequences at a desired sequence pattern. In order to do this, it should be noted that in principle it is possible to identify the sequence of nucleotides that went through the pore. This can be done by detecting voltage signals such as capacitance changes or tunneling current due to the presence of one or more nucleotides in the proximity of strategically located sensors within the nanopore during the "stop" phase of the translocation. After a desired DNA sequence pattern is detected, the DNA molecule can be stopped by applying the trapping potential for a long time. Under this condition, DNA can be electrically stretched and broken into two pieces at a pre-determined location within the DNA transistor using the features described herein in accordance with exemplary embodiments. After cutting the DNA, the DNA fragment closer to the exit of the pore can be electrically driven through the nanopore to exit the membrane.

For example, exemplary embodiments disclose a device 100 (shown in FIG. 1) that cuts a DNA molecule (or any linear charged polymer) at a prescribed length and/or at a prescribed sequence pattern by means of the application of electrical voltages within the DNA transistor, thus allowing the device to act as "DNA electric scissors". Note that cutting DNA with DNA electric scissors does not require complicated sample preparations or expensive enzymes. The cost to electrically "cut" long DNA into small fragments of controlled size and/or at predetermined sequences is expected to be substantially lower than the cost involved in traditional methods. Note also that while some restriction enzymes cut sequences at specific DNA sequences in single stranded DNA, the restriction enzymes seem to do so at transient double stranded regions formed by hybridization of complementary sequences within the same single stranded molecule. In this respect, the DNA scissors of exemplary embodiments in the mode in which they cut DNA molecules at specific sequence patterns do so in single stranded DNA molecules without the need of the complementary strand within the same molecule in accordance with exemplary embodiments.

Now turning to FIG. 1 in detail, FIG. 1 illustrates the cross-section of a device 100 having a long DNA in a DNA transistor in accordance with exemplary embodiments. It is noted that the device 100 is not drawn to scale but is drawn to illustrate various features as understood by one skilled in the art. A membrane 120, which is made of films 101, 102, 103, 104, and 105, partitions a reservoir 106 into two parts.

A nanometer size hole 107, referred to as a nanopore, is made through the membrane 120. The reservoir 106 and the hole 107 are then filled with ionic buffer 108. The ionic buffer 108 may be a salt and water solution.

The reservoir 106 may be an insulated container that is configured to hold the solution of the conductive ionic buffer 108. The membrane parts 101, 103, and 105 are made of electrically conducting materials, while membrane part 102 and 104 are made of insulating materials. The voltage bias 109 is applied between membrane parts 101 and 103 with the direction defined by the battery sign. Likewise, the voltage bias 110 is applied between membrane parts 103 and 105 with the direction defined by the battery sign. A polymer, such as a DNA molecule 111, with discrete charges 112 can be driven into the nanopore 107 by applying a voltage bias 113 through two electrodes 114 and 115, which are immersed in the two parts of the ionic buffers 108.

The translocation of the DNA molecule 111 can be precisely controlled at a single-base resolution by applying the proper voltages 109 and 110 on and off. By the voltage biases 109 and 110, electric fields 122 and 124 (in the regions of 102 and 104) are produced to interact with the discrete charges 112 of the DNA molecule 111 (in the regions of 102 and 104). When the DNA molecule 111 moves downward, there is an imbalance of forces on the DNA molecule 111 in the regions 102 and 104, and the net force on the DNA molecule 111 is upward. Conversely, when the DNA molecule 111 moves upward the electric fields 122 and 124 create an imbalance of forces on the DNA molecule 111, and the net force on the DNA molecule 111 is downward. Thus, the voltages 109 and 110 will trap the DNA molecule 111 at the minimal of a trapping potential well when the electric fields 122 and 124 cause the forces on the DNA molecule 111 to be balanced. For example, the voltages 109 and 110 can keep the DNA molecule 111 in place like a steady state and cause a tug of war between the forces on the DNA molecule 111 so that the DNA molecule 111 remains still in the nanopore 107. For further information regarding controlling a DNA molecule, reference is made to "Nanopore in metal-dielectric sandwich for DNA position control" in Applied Physics Letters 91, 153103 (2007) by Stas Polonsky, Steve Rossnagel, and Gustavo Stolovitzky, which is herein incorporated by reference.

The thicknesses of the insulating layers 102 and 104 and the conductive layer 103 should be properly chosen to be commensurate with the spacing between neighboring phosphate groups in the DNA molecule 111. As one example in exemplary embodiments, a rule of thumb that may be utilized (but not an essential configuration) is one in which the thickness of each insulating layer 102 and 104 is equal to (n+0.5)d and the thickness of the middle conductive layer 103 is equal to md, where m and n are small integers (e.g., between 2 and 10) and where d is the spacing between neighboring phosphate groups in the DNA molecule 111. Accordingly, the thickness of the insulating layers 102 and 104 and the thickness of the middle conductive layer 103 may be (but are not limited to) a function of the spacing d between the phosphate groups in the DNA molecule 111 being cut according to exemplary embodiments.

It is understood by one skilled in the art that double stranded DNA consists of two long polymers of simple units called nucleotides, with backbones made of sugars and phosphate groups joined by ester bonds. These two strands run in opposite directions to each other and are therefore anti-parallel. Attached to each sugar is one of four types of molecules called bases. It is the sequence of these four bases along the backbone that encodes biological information.

In accordance with exemplary embodiments, there are three operational stages during a DNA-cutting cycle. As shown in FIG. 1, the electric fields 122 and 124 in the insulating layers 102 and 104 have the same strength but opposite directions. Note that the representation of the electric fields 122 and 124 is shown on the right side of FIGS. 1 and 2 so as not to obscure the drawings, but it is understood that the electric fields 122 and 124 are across the films 102 and 104 to interact with the DNA molecule 111. Each time the voltages 109 and 110 switch from +V to −V in the presence of a biasing electric voltage 113 from the top to the bottom (trans to cis) of the compartment of the reservoir 106, the DNA strand 111 is driven from the top compartment by half a spacing between neighboring phosphate groups due to the swapping of the maximum and minimum of the electrical trapping energy of the DNA molecule 111. If this switching (from +V to −V of the voltages 109 and 110) is done periodically, the translocation will be at a rate of one base per period. After the DNA molecule 111 advances a prescribed length (and/or if the DNA molecule 111 is simultaneously being sequenced until the right sequence is identified), the cycling stops (from +V to −V of the voltages 109 and 110), and the voltages 109 and 110 are set to maintain, e.g., a voltage having a magnitude of V. Under this configuration the DNA molecule 111 is trapped in the nanopore 107. In exemplary embodiments, the typical but not limiting value of V for trapping DNA is about 1 or 2 volts.

Figure 2:
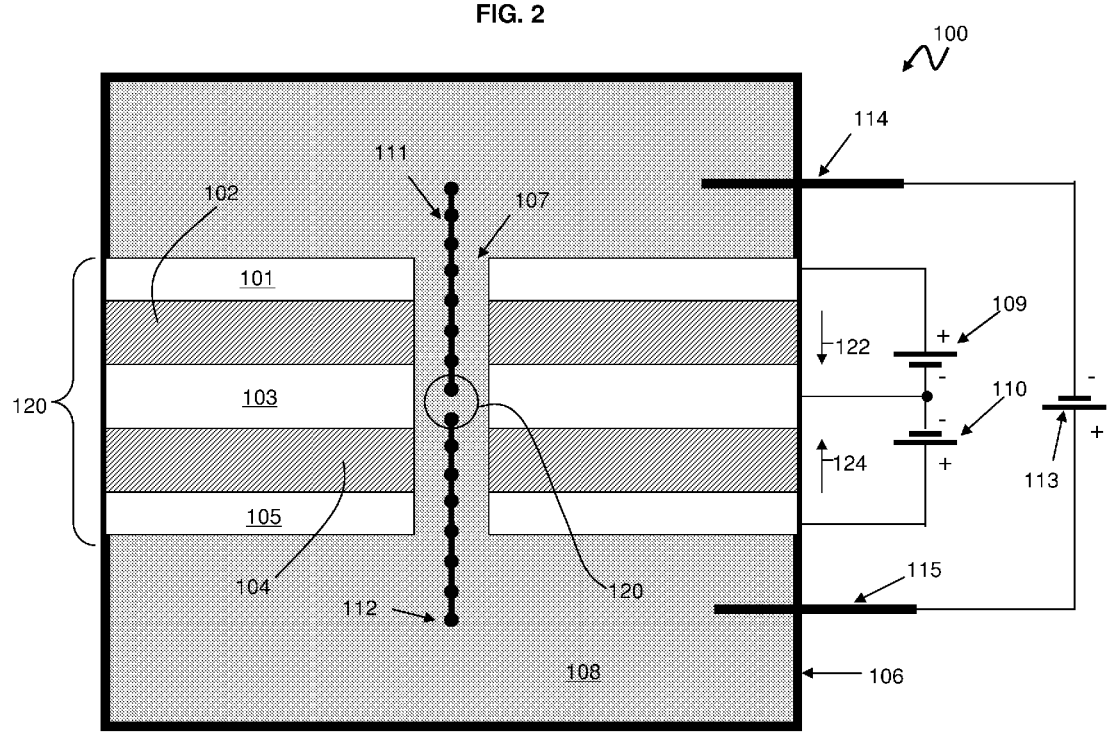

With reference to FIG. 2, the electric fields 122 and 124 in the insulating layers 102 and 104 respectively point downwards and upwards, and the DNA molecule 111 is slightly stretched by the electric fields 122 and 124 in exemplary embodiments. The electric fields 122 and 124 pointing toward each other may be increased (by increasing respective voltages 109 and 110), and the electric fields 122 and 124 pointing toward each other exert forces on the DNA fragments (in two electric field regions) in opposite directions, pulling the two DNA fragments away from each other. In other words, although the electric fields 122 and 124 point toward each other, the combination of forces interacting on the DNA molecule 111 stretch the DNA molecule 111 to cause the cut, which is illustrated at location 120. For example, one electric field region is the area around the insulating layer 102 and the other electric field region is the area around the insulating layer 104; the DNA fragments (or portions) of the DNA molecule 111 that are in those electric field regions have forces that cause the DNA fragment (portion) in one electric field region to pull away from the DNA fragment (portion) in the other electric field region.

Further, in the DNA-cutting mode, an additional voltage pulse $V'=V_0$ is added to voltages 109 and 110 for a duration δ in accordance with exemplary embodiments. When $V_0>4$ volts, the stretching force on the DNA molecule 111 is equal to $F=e(V+V_0)/d>1$ nN, which is strong enough to break the DNA backbone of the DNA molecule 111 near electrode 103 (identified by the circle 120). In the equation above, e is one electron charge (corresponding to the charge of one nucleotide of the DNA molecule 111), d is the spacing between the negative charges 112 (of the phosphate groups) of the DNA molecule 111, V is the trapping voltage, and $V_0$ is the cutting voltage needed to cut the DNA molecule 111 as shown in FIG. 2. Also, nN is a nanonewton. Note that the voltage pulse is only applied for a time δ in order to avoid possible electrochemical reactions when applying a high voltage on the electrodes 114 and 115. In addition, although $V_0>4$ is provided as an example voltage to cut the DNA molecule 111, the value of $V_0$ is not meant to be limiting and other values for $V_0$ may be utilized in accordance the present disclosure as understood by one skilled in the art.

Additionally, in exemplary embodiments, the location 120 of the break to cut the DNA molecule 111 can be tuned by making the thickness of the metal layer 103 smaller. Since the DNA molecule 111 is cut in the location 120 at the metal layer (film) 103, the metal layer 103 can be made smaller to provide a more precise cut of the DNA molecule 111.

Figure 5:
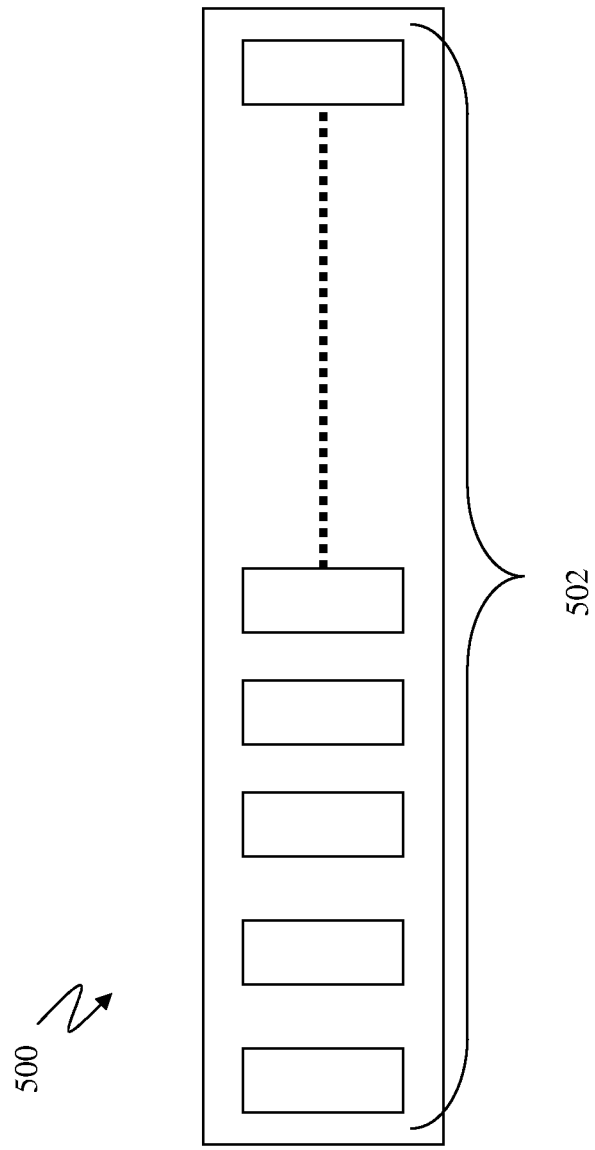
FIG. 5 illustrates a library of DNA fragments (or any linear charged polymer) in accordance with exemplary embodiments.

Now turning to FIG. 5, FIG. 5 illustrates a library 500 of DNA fragments (or any linear charged polymer) in accordance with exemplary embodiments. The library 500 is a collection of DNA fragments that is physically stored in a solution in containers 502, and the containers 502 may be any container capable of storing DNA as understood by one skilled in the art. For example, the DNA fragments may be stored in a test tube.

In accordance with exemplary embodiments, the device 100 can cut the DNA molecule 111 into many different DNA fragments of different lengths, and the DNA fragments can be organized and stored in the library 500. The DNA fragments can be cut into different lengths and stored in the container 502.

For example, a user of the device 100 may cut the DNA molecule 111 into the desired sizes (i.e., lengths of the DNA fragments) and monitor the cutting process. The user of the device 100 may cut the DNA fragments into a proportion of different lengths as desired for storage in the container 502. For example, in each container 502, for each DNA fragment of length 100, there may be 2 DNA fragments of length 135, 7 DNA fragments of length 250, and so on. Accordingly, utilizing the device 100, the user can cut and store (in each container 502 of the library 500) DNA fragments in an arbitrary desired proportion, and/or with any desired distribution of sizes.

FIG. 3 illustrates a method 300 for cutting linear charged polymers inside a nanopore in accordance with exemplary embodiments.

A first voltage (such as the voltage 109) is applied to create an electric field (such as the electric field 122) in a first direction at operation 302.

A second voltage (such as the voltage 110) is applied to create an electric field (such as the electric field 124) in a second direction at operation 304. The first direction is opposite to the second direction.

When the electric field in the first direction and the electric field in the second direction are applied to a linear charged polymer (such as the DNA molecule 111) inside the nanopore 107, the electric fields cause the linear charged polymer 111 to be cut at a precise location (such as the location 120) at operation 306.

Further, a third voltage (such as the voltage 113) is applied to be a biasing voltage that moves the linear charged polymer 111 inside the nanopore 107. Cutting the linear charged polymer 111 at the precise location 120 comprises stretching the linear charged polymer 111 until the linear charged polymer 111 breaks at the precise location 120. When the electric field 122 in the first direction and the electric field 124 in the second direction are applied to the linear charged polymer 111 inside the nanopore 107 to cause the linear charged polymer 111 to be cut at the precise location 120, the linear charged polymer 111 is cut into pieces at every predetermined length. The predetermined length to cut the linear charged polymer 111 may be, e.g., every X amount of units. For example, the linear charged polymer 111 may be cut within a predetermined accuracy, such as every 100 nucleotides plus or minus 5 nucleotides. That is, the linear charged polymer 111 may be cut every certain number of nucleotides within a certain accuracy as desired. The Each unit in the DNA molecule 111 may correspond to each charge 112 in the phosphate group, and the DNA molecule 111 can be cut every X number of charges 112. Also, the linear charged polymer 111 can be cut at a predetermined distance based on a particular pattern of monomers.

The linear charged polymer 111 is not meant to be limiting and may comprise a cationic polysaccharide, deoxyribonucleic acid (DNA), ribonucleic acid (RNA), and/or other polymers. In accordance with exemplary embodiments, both the first voltage and the second voltage are applied such that the electric field in the first direction and the electric field in the second direction are strong enough to break the linear charged polymer 111 at the precise location 120.

It is understood by one skilled in the art that a polymer is a large molecule (macromolecule) composed of repeating structural units typically connected by covalent chemical bonds and in exemplary embodiments, the polymer can be cut every X repeating units. Due to the extraordinary range of properties accessible in polymeric materials, they have come to play an essential and ubiquitous role in everyday life, from plastics and elastomers on the one hand to natural biopolymers such as DNA and proteins that are essential for life on the other. A simple example is polyethylene, whose repeating unit is based on ethylene monomer. Most commonly, as in this example, the continuously linked backbone of a polymer used for the preparation of plastics consists mainly of carbon atoms. However, the backbone of DNA is in fact based on a phosphodiester bond, and repeating units of polysaccharides (e.g. cellulose) are joined together by glycosidic bonds via oxygen atoms.

Figure 4:
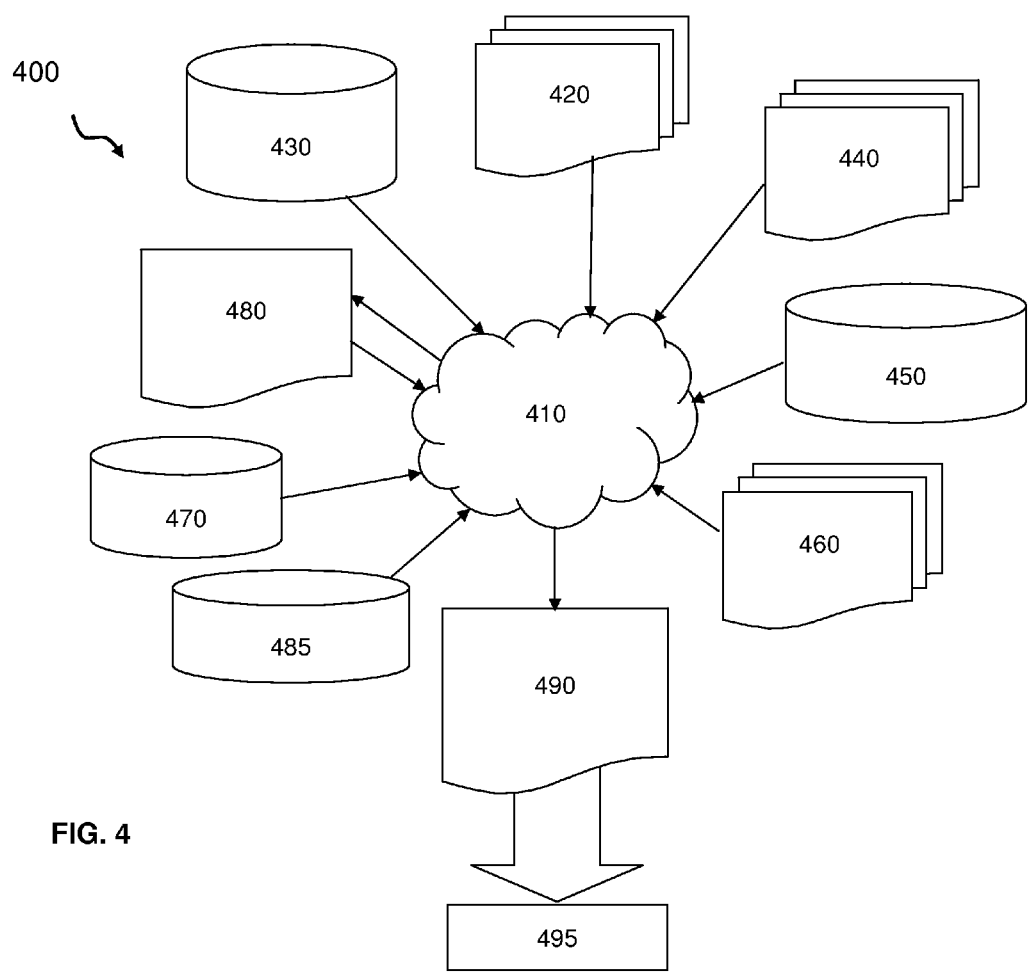
FIG. 4 shows a block diagram of an exemplary design flow used for example, in semiconductor IC logic design, simulation, test, layout, and manufacture of exemplary embodiments.

FIG. 4 shows a block diagram of an exemplary design flow 400 used for example, in semiconductor IC logic design, simulation, test, layout, and manufacture. Design flow 400 includes processes, machines and/or mechanisms for processing design structures or devices to generate logically or otherwise functionally equivalent representations of the design structures and/or devices described above and shown in FIGS. 1 and 2. The design structures processed and/or generated by design flow 400 may be encoded on machine-readable transmission or storage media to include data and/or instructions that when executed or otherwise processed on a data processing system generate a logically, structurally, mechanically, or otherwise functionally equivalent representation of hardware components, circuits, devices, or systems. Machines include, but are not limited to, any machine used in an IC design process, such as designing, manufacturing, or simulating a circuit, component, device, or system. For example, machines may include: lithography machines, machines and/or equipment for generating masks (e.g. e-beam writers), computers or equipment for simulating design structures, any apparatus used in the manufacturing or test process, or any machines for programming functionally equivalent representations of the design structures into any medium (e.g. a machine for programming a programmable gate array).

Design flow 400 may vary depending on the type of representation being designed. For example, a design flow 400 for building an application specific IC (ASIC) may differ from a design flow 400 for designing a standard component or from a design flow 400 for instantiating the design into a programmable array, for example a programmable gate array (PGA) or a field programmable gate array (FPGA) offered by Altera® Inc. or Xilinx® Inc.

FIG. 4 illustrates multiple such design structures including an input design structure 420 that is preferably processed by a design process 410. Design structure 420 may be a logical simulation design structure generated and processed by design process 410 to produce a logically equivalent functional representation of a hardware device. Design structure 420 may also or alternatively comprise data and/or program instructions that when processed by design process 410, generate a functional representation of the physical structure of a hardware device. Whether representing functional and/or structural design features, design structure 420 may be generated using electronic computer-aided design (ECAD) such as implemented by a core developer/designer. When encoded on a machine-readable data transmission, gate array, or storage medium, design structure 420 may be accessed and processed by one or more hardware and/or software modules within design process 410 to simulate or otherwise functionally represent an electronic component, circuit, electronic or logic module, apparatus, device, or system such as those shown in FIGS. 1 and 2. As such, design structure 420 may comprise files or other data structures including human and/or machine-readable source code, compiled structures, and computer-executable code structures that when processed by a design or simulation data processing system, functionally simulate or otherwise represent circuits or other levels of hardware logic design. Such data structures may include hardware-description language (HDL) design entities or other data structures conforming to and/or compatible with lower-level HDL design languages such as Verilog and VHDL, and/or higher level design languages such as C or C++.

Design process 410 preferably employs and incorporates hardware and/or software modules for synthesizing, translating, or otherwise processing a design/simulation functional equivalent of the components, circuits, devices, or logic structures shown in FIGS. 1 and 2 to generate a netlist 480 which may contain design structures such as design structure 420. Netlist 480 may comprise, for example, compiled or otherwise processed data structures representing a list of wires, discrete components, logic gates, control circuits, I/O devices, models, etc. that describes the connections to other elements and circuits in an integrated circuit design. Netlist 480 may be synthesized using an iterative process in which netlist 480 is resynthesized one or more times depending on design specifications and parameters for the device. As with other design structure types described herein, netlist 480 may be recorded on a machine-readable data storage medium or programmed into a programmable gate array. The medium may be a non-volatile storage medium such as a magnetic or optical disk drive, a programmable gate array, a compact flash, or other flash memory. Additionally, or in the alternative, the medium may be a system or cache memory, buffer space, or electrically or optically conductive devices and materials on which data packets may be transmitted and intermediately stored via the Internet, or other networking suitable means.

Design process 410 may include hardware and software modules for processing a variety of input data structure types including netlist 480. Such data structure types may reside, for example, within library elements 430 and include a set of commonly used elements, circuits, and devices, including models, layouts, and symbolic representations, for a given manufacturing technology (e.g., different technology nodes, 32 nm, 45 nm, 90 nm, etc.). The data structure types may further include design specifications 440, characterization data 450, verification data 460, design rules 470, and test data files 485 which may include input test patterns, output test results, and other testing information. Design process 410 may further include, for example, standard mechanical design processes such as stress analysis, thermal analysis, mechanical event simulation, process simulation for operations such as casting, molding, and die press forming, etc. One of ordinary skill in the art of mechanical design can appreciate the extent of possible mechanical design tools and applications used in design process 410 without deviating from the scope and spirit of the invention. Design process 410 may also include modules for performing standard circuit design processes such as timing analysis, verification, design rule checking, place and route operations, etc. Design process 410 employs and incorporates logic and physical design tools such as HDL compilers and simulation model build tools to process design structure 420 together with some or all of the depicted supporting data structures along with any additional mechanical design or data (if applicable), to generate a second design structure 490. Design structure 490 resides on a storage medium or programmable gate array in a data format used for the exchange of data of mechanical devices and structures (e.g. information stored in a IGES, DXF, Parasolid XT, JT, DRG, or any other suitable format for storing or rendering such mechanical design structures). Similar to design structure 420, design structure 990 preferably comprises one or more files, data structures, or other computer-encoded data or instructions that reside on transmission or data storage media and that when processed by an ECAD system generate a logically or otherwise functionally equivalent form of one or more of the embodiments of the invention shown in FIGS. 1 and 2. In one embodiment, design structure 490 may comprise a compiled, executable HDL simulation model that functionally simulates the devices shown in FIGS. 1 and 2.

Design structure 490 may also employ a data format used for the exchange of layout data of integrated circuits and/or symbolic data format (e.g. information stored in a GDSII (GDS2), GL1, OASIS, map files, or any other suitable format for storing such design data structures). Design structure 490 may comprise information such as, for example, symbolic data, map files, test data files, design content files, manufacturing data, layout parameters, wires, levels of metal, vias, shapes, data for routing through the manufacturing line, and any other data required by a manufacturer or other designer/developer to produce a device or structure as described above and shown in FIGS. 1 and 2. Design structure 490 may then proceed to a stage 495 where, for example, design structure 490: proceeds to tape-out, is released to manufacturing, is released to a mask house, is sent to another design house, is sent back to the customer, etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the exemplary embodiments to the invention have been described, it will be understood that those skilled in the art, both now and in the future, may make various improvements and enhancements which fall within the scope of the claims which follow. These claims should be construed to maintain the proper protection for the invention first described.

What is claimed is:

1. A method for cutting a single strand DNA molecule inside a nanopore, comprising:
    applying a first voltage to create an electric field in a first direction;
    applying a second voltage to create an electric field in a second direction, wherein the first direction is opposite to the second direction on the single strand DNA molecule; and
    when the electric field in the first direction and the electric field in the second direction are applied to the single strand DNA molecule inside a nanopore, causing the single strand DNA molecule to be cut at a location within a predetermined precision on the single strand DNA molecule inside the nanopore.

2. The method of claim 1, further comprising applying a third voltage to be a biasing voltage that moves the single strand DNA molecule inside the nanopore.

3. The method of claim 1, wherein the causing the single strand DNA molecule to be cut at the location comprises stretching the single strand DNA molecule until the single strand DNA molecule breaks at the location within a predetermined precision.

4. The method of claim 1, wherein when the electric field in the first direction and the electric field in the second direction are applied to the single strand DNA molecule inside the nanopore and causes the single strand DNA molecule to be cut at the location, the single strand DNA molecule is cut into pieces at every predetermined length.

5. The method of claim 1, wherein when the electric field in the first direction and the electric field in the second direction is applied to the single strand DNA molecule inside the nanopore and causes the single strand DNA molecule to be cut at the location, the single strand DNA molecule is cut at a predetermined distance based on a particular pattern of monomers.

6. The method of claim 1, wherein when the electric field in the first direction and the electric field in the second direction are applied to the single strand DNA molecule inside the nanopore and causes the single strand DNA molecule to be cut at the location, the single strand DNA molecule is cut between two monomers of the backbone of the single strand DNA molecule.

7. The method of claim 1, wherein both the first voltage and the second voltage are applied such that the electric field in the first direction and the electric field in the second direction are strong enough to stretch and break the single strand DNA molecule itself at the location;
    wherein the single strand DNA molecule is not a double strand.

8. The method of claim 1, wherein when the electric field in the first direction and the electric field in the second direction are applied to the single strand DNA molecule inside the nanopore and causes the single strand DNA molecule to be cut at the precise location, the single strand DNA molecule is cut between consecutive charges of a backbone of the single strand DNA molecule.

* * * * *